US00PP23820P2

(12) United States Plant Patent
Heuger

(10) Patent No.: US PP23,820 P2
(45) Date of Patent: Aug. 6, 2013

(54) ***HELLEBORUS* PLANT NAMED 'HLR 190'**

(50) Latin Name: *Helleborus hybridus*
Varietal Denomination: HLR 190

(76) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 13/385,161

(22) Filed: Feb. 6, 2012

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Annette Para
(74) *Attorney, Agent, or Firm* — C. A. Whealy

(57) ABSTRACT

A new and distinct cultivar of *Helleborus* plant named 'HLR 190', characterized by its upright and mounded plant habit; uniform flowering habit; dark green-colored leaves; long flowering period; semi-double red purple to greyed purple-colored flowers; and good garden performance.

2 Drawing Sheets

Botanical designation: *Helleborus hybridus.*
Cultivar denomination: 'HLR 190'.

BACKGROUND OF THE INVENTION

The present invention relates to a new and distinct cultivar of *Helleborus* plant, botanically known as *Helleborus hybridus*, and hereinafter referred to by the name 'HLR 190'.

The new *Helleborus* plant is a product of a planned breeding program in Glandorf, Germany. The objective of the breeding program was to create new uniform *Helleborus* plants with unique and attractive plant habit, leaf and flower coloration and resistance to pests.

The new *Helleborus* plant originated from a cross-pollination conducted by the Inventor in Glandorf, Germany in February, 2006 of an unnamed proprietary seedling selection of *Helleborus hybridus*, not patented, as the female, or seed, parent with an unnamed proprietary seedling selection of *Helleborus hybridus*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in October, 2007.

Asexual reproduction of the new *Helleborus* plant by divisions in a controlled greenhouse environment in Glandorf, Germany since February, 2008 has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'HLR 190'. These characteristics in combination distinguish 'HLR 190' as a new and distinct *Helleborus* plant:

1. Upright and mounded plant habit.
2. Uniform flowering habit.
3. Dark green-colored leaves.
4. Long flowering period.
5. Semi-double red purple to greyed purple-colored flowers.
6. Good garden performance.

Compared to plants of the parent selections, plants of the new *Helleborus* are more uniformly mounded and are more uniformly and freely flowering.

Plants of the new *Helleborus* can be compared to plants of *Helleborus hybridus*×*Helleborus hybridus* 'HLR 160', disclosed in U.S. Plant Pat. No. 21,504. In side-by-side comparisons conducted in Glandorf, Germany, plants of the new *Helleborus* differed from plants of 'HLR 710' in flower type and color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'HLR 190' grown in a container.

The photograph on the second sheet is a close-up view of a typical flower of 'HLR 190'.

DETAILED BOTANICAL DESCRIPTION

The aforementioned photographs and following observations, measurements and values describe plants grown during the winter in 15-cm containers in a glass-covered greenhouse in Glandorf, Germany and under environmental conditions and cultural practices which closely approximate commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus hybridus*×*Helleborus hybridus* 'HLR 190'.

Parentage:

*Female, or seed, parent*.—Unnamed proprietary seedling selection of *Helleborus hybridus*, not patented.

*Male, or pollen, parent*.—Unnamed proprietary seedling selection of *Helleborus hybridus*, not patented.

Propagation:

*Type*.—By tissue culture.

*Time to initiate roots*.—About two months at 12° C.

*Time to produce a rooted young plant*.—About six months at 4° C. to 15° C.

*Root description*.—Thick to thin, fleshy; white to brown in color.

*Rooting habit*.—Sparse.

Plant description:

*Plant form and growth habit*.—Herbaceous perennial; upright and mounding plant habit with flowers held just above the foliar plane; plant shape is globular; moderately vigorous growth habit.

*Plant height*.—About 38.7 cm.

*Plant diameter* (*area of spread*).—About 50.8 cm.

Foliage description:

*Arrangement*.—Leaves arranged in a basal rosette; leaves palmately compound with five leaflets per leaf.

*Leaf length*.—About 19 cm.

*Leaf width*.—About 20.8 cm.

*Leaflet length*.—About 11.7 cm.

*Leaflet width*.—About 3.5 cm.

*Leaf shape*.—Palmate; orbicular in outline.

*Leaflet shape*.—Narrowly elliptic to narrowly obovate.

*Leaflet apex*.—Acute.

*Leaflet base*.—Attenuate.

*Leaflet margin*.—Sharply serrate; moderately undulate.

*Leaflet texture, upper and lower surfaces*.—Smooth, glabrous; leathery.

*Leaflet venation pattern*.—Pinnate.

*Leaflet color*.—Developing leaves, upper and lower surfaces: Close to 144A. Fully developed leaves, upper surface: Close to N137B; venation, close to 144C. Fully developed leaves, lower surface: Close to 146B; venation, close to 144C.

*Petiole*.—Length: About 15.8 cm. Diameter: About 4 mm. Texture, upper and lower surfaces: Smooth, glabrous. Color, upper and lower surfaces: Close to 144C.

Flower description:

*Flower shape and habit*.—Semi-double rotate flowers arranged in terminal and axillary cymes; uniform flowering habit with about four flowers and flower buds developing per terminal inflorescence; flowers nodding.

*Fragrance*.—None detected.

*Natural flowering season*.—Plants begin flowering about ten months after planting; long flowering period, plants flower from late winter to early spring in Germany.

*Flower longevity on the plant*.—About ten days; flowers not persistent.

*Flower buds*.—Length: About 2.6 cm. Diameter: About 1.4 cm. Shape: Ovate. Color: Close to 144B to 144C; towards the apex, strongly tinged with close to 186C to 186D.

*Inflorescence height*.—About 45 cm.

*Inflorescence diameter*.—About 23.5 cm.

*Flower diameter*.—About 7.1 cm.

*Flower depth* (*height*).—About 4 cm.

*Petals*.—None observed on plants of the new *Helleborus*.

*Sepals*.—Quantity and arrangement: Five arranged in a single whorl. Length: About 3.9 cm. Width: About 2.9 cm. Shape: Elliptic. Apex: Abruptly acute. Margin: Entire, undulate. Texture, upper and lower surfaces: Smooth, glabrous. Color: When opening, upper surface: Between 187B to 187C and 59A dotted with close to N186C. When opening, lower surface: Slightly darker than between 64A and N77B. Fully opened, upper surface: Between 187B to 187C and 59A dotted with close to N186C; with development, color becoming closer to 148B dotted with close to 187C. Fully opened, lower surface: Slightly darker than between 64A and N77B.

*Sepaloids*.—Quantity and arrangement: About 15 arranged in several whorls. Length: About 3.3 cm. Width: About 1.7 cm. Shape: Elliptic. Apex: Abruptly acute. Margin: Entire, undulate. Texture, upper and lower surfaces: Smooth, glabrous. Color: When opening, upper surface: Between 187B to 187C and 59A dotted with close to N186C. When opening, lower surface: Slightly darker than between 64A and N77B. Fully opened, upper surface: Between 187B to 187C and 59A dotted with close to N186C; with development, color becoming closer to 148B dotted with close to 187C. Fully opened, lower surface: Slightly darker than between 64A and N77B.

*Peduncles*.—Strength: Moderately strong. Length: About 35.2 cm. Diameter: About 6 mm. Aspect: About 30° from vertical. Texture: Smooth, glabrous. Color: Close to 145C to 145D.

*Pedicels*.—Strength: Moderately strong. Length: About 4.1 cm. Diameter: About 2 mm. Aspect: Erect to about 30° from the peduncle axis. Texture: Smooth, glabrous. Color: Close to 145B.

*Reproductive organs*.—Stamens: Quantity per flower: About 80. Filament length: About 1.5 cm. Filament color: Close to 157A. Anther shape: Reniform. Anther length: About 1.5 mm. Anther color: Close to 150D. Pollen amount: Scarce. Pollen color: Close to 158D. Pistils: Quantity per flower: About five. Pistil length: About 1.4 cm. Stigma shape: Club-shaped. Stigma color: Close to 145D. Style length: About 1.3 cm. Style color: Close to 186C. Ovary color: Close to 145C. Nectaries (transformed petals): None observed on plants of the new *Helleborus*. Seeds and fruits: Seed and fruit development have not been observed on plants of the new *Helleborus*.

Garden performance: Plants of the new *Helleborus* have been observed to have good garden performance and to tolerate rain and wind; plants of the new *Helleborus* have been observed to tolerate high temperatures of about 35° C. and are hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'HLR 190' as illustrated and described.

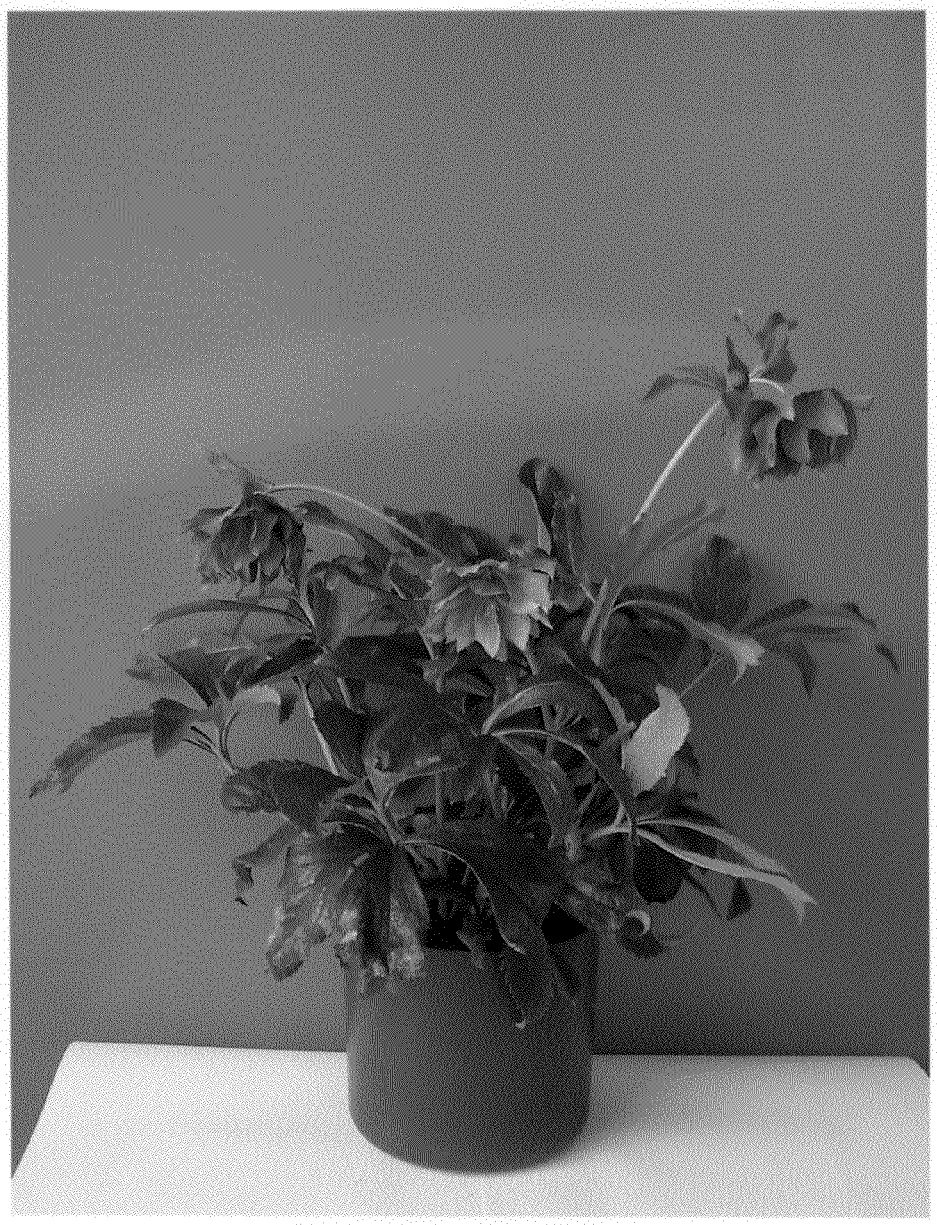

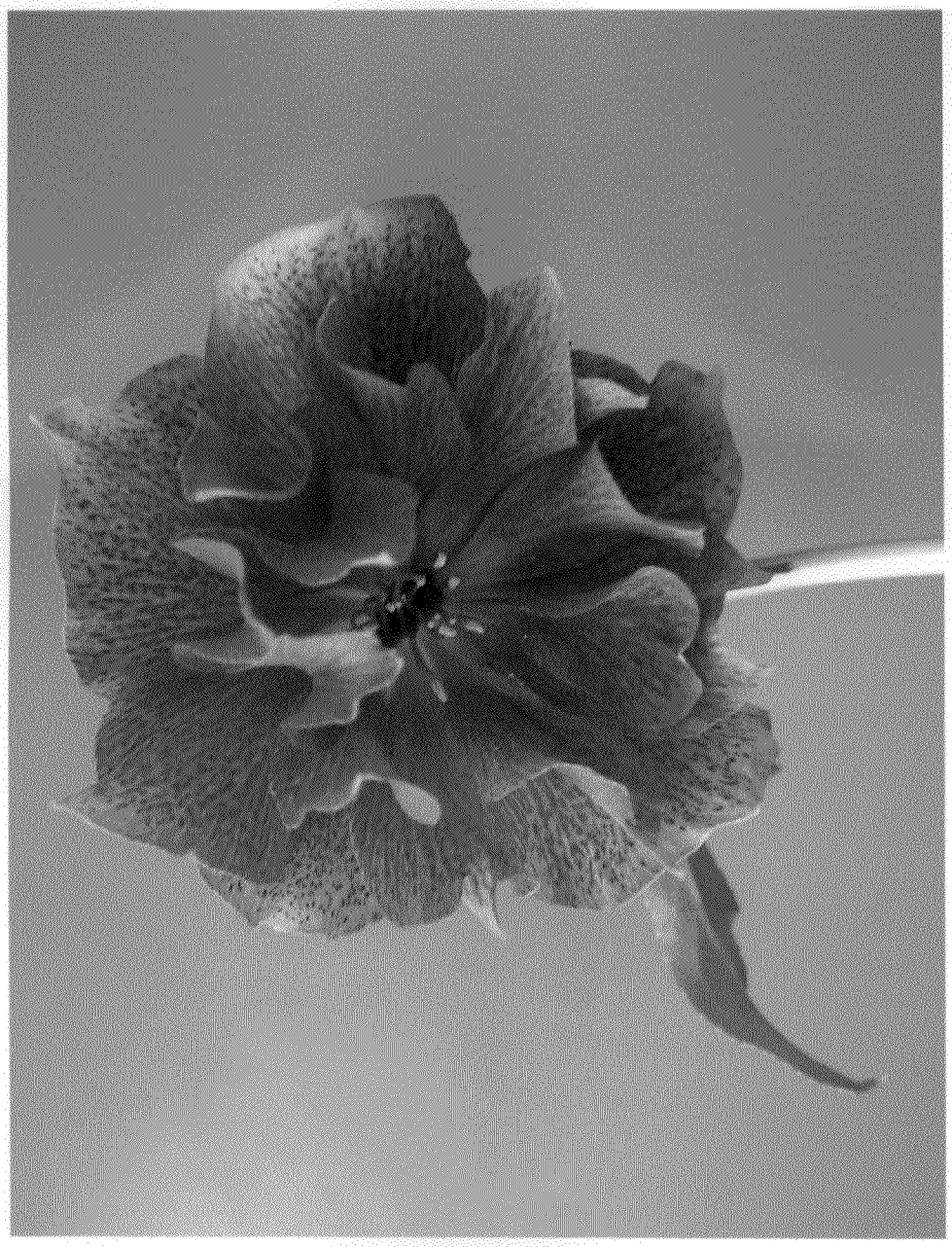

* * * * *